United States Patent
Schan et al.

(10) Patent No.: US 11,337,600 B2
(45) Date of Patent: May 24, 2022

(54) ENDOSCOPE

(71) Applicant: Scholly Fiberoptic GmbH, Denzlingen (DE)

(72) Inventors: Dieter Schan, Rastatt (DE); Tilman Stahle, Freiburg (DE); Markus Bleiziffer, Freiburg (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 831 days.

(21) Appl. No.: 15/417,369

(22) Filed: Jan. 27, 2017

(65) Prior Publication Data
US 2017/0215718 A1     Aug. 3, 2017

(30) Foreign Application Priority Data
Jan. 30, 2016 (DE) .......................... 102016001048.7

(51) Int. Cl.
*A61B 1/12* (2006.01)
*A61B 1/00* (2006.01)
*A61B 1/05* (2006.01)

(52) U.S. Cl.
CPC .......... *A61B 1/127* (2013.01); *A61B 1/00193* (2013.01); *A61B 1/05* (2013.01); *A61B 1/051* (2013.01); *A61B 1/128* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,241,363 A | * | 8/1993 | Garner | B01L 3/021 356/244 |
| 5,605,532 A | * | 2/1997 | Schermerhorn | A61B 1/0008 600/169 |
| 8,206,288 B2 | | 6/2012 | Wieters et al. | |
| 2005/0109768 A1 | * | 5/2005 | Aoki | H05B 3/265 219/543 |
| 2007/0149856 A1 | * | 6/2007 | Segawa | A61B 1/051 600/169 |
| 2008/0073517 A1 | * | 3/2008 | Melville | G02B 7/008 250/306 |
| 2009/0092364 A1 | * | 4/2009 | Johnston | A61B 1/00096 385/117 |
| 2010/0010313 A1 | * | 1/2010 | Muckner | A61B 1/0008 600/169 |
| 2010/0016671 A1 | * | 1/2010 | Wieters | A61B 1/0008 600/169 |
| 2010/0185052 A1 | * | 7/2010 | Chang | A61B 1/0011 600/112 |
| 2010/0309553 A1 | * | 12/2010 | Nagamizu | A61B 1/04 359/512 |

(Continued)

FOREIGN PATENT DOCUMENTS

DE     1572651     3/1970

*Primary Examiner* — Timothy J Neal
*Assistant Examiner* — Genja M Frankert
(74) *Attorney, Agent, or Firm* — Volpe Koenig

(57) ABSTRACT

An endoscope (1) having a heating device (7) with at least one stiffened area (9, 10, 27) on a printed circuit board (8). At least one heating element (11) of the heating device is arranged in the stiffened area (9, 10, 27), and the heating device (7) is laid flat, from the outside, on a metallic head part (4) at the distal end (3) of the endoscope.

19 Claims, 2 Drawing Sheets

(56) References Cited

U.S. PATENT DOCUMENTS

| | | | |
|---|---|---|---|
| 2011/0092769 A1* | 4/2011 | Kokubo | A61B 1/127 600/109 |
| 2012/0172767 A1* | 7/2012 | Honda | A61B 17/320068 601/3 |
| 2014/0088366 A1* | 3/2014 | Solingen | A61B 1/00135 600/169 |
| 2014/0221743 A1* | 8/2014 | Sugiyama | A61B 1/128 600/109 |
| 2015/0228678 A1* | 8/2015 | Yoshida | A61B 1/00071 600/110 |
| 2015/0238072 A1* | 8/2015 | Makmel | A61B 1/00163 219/221 |
| 2015/0297070 A1* | 10/2015 | Ide | A61B 1/127 600/103 |
| 2015/0313454 A1* | 11/2015 | Ide | A61B 1/0008 600/129 |
| 2017/0118835 A1* | 4/2017 | Badia | H05K 1/0281 |
| 2018/0296076 A1* | 10/2018 | Yoshida | G02B 23/2484 |

* cited by examiner

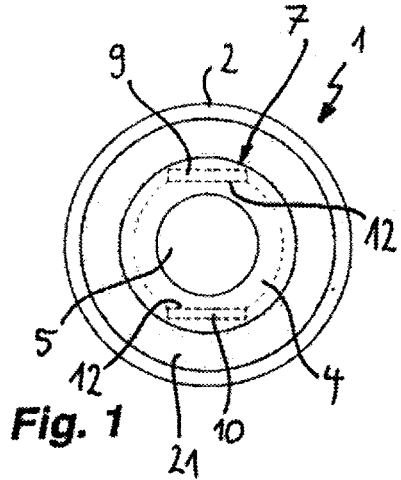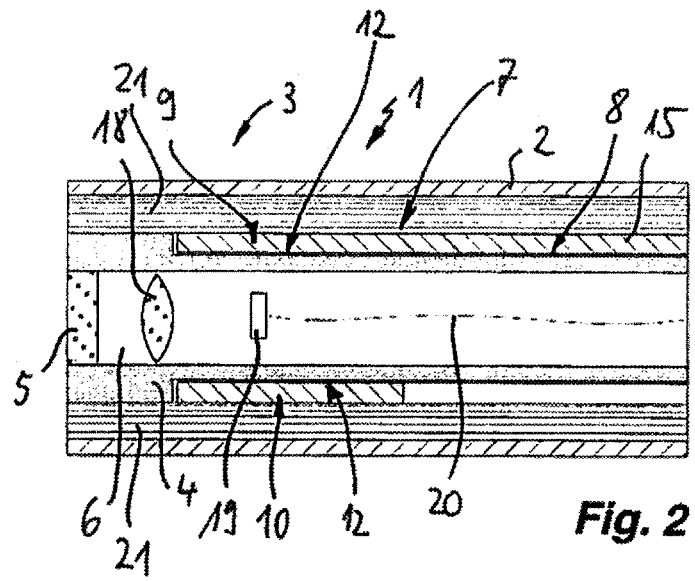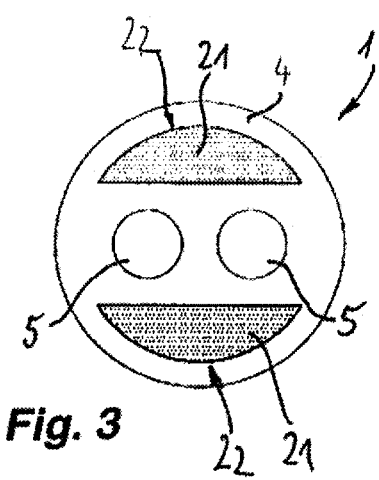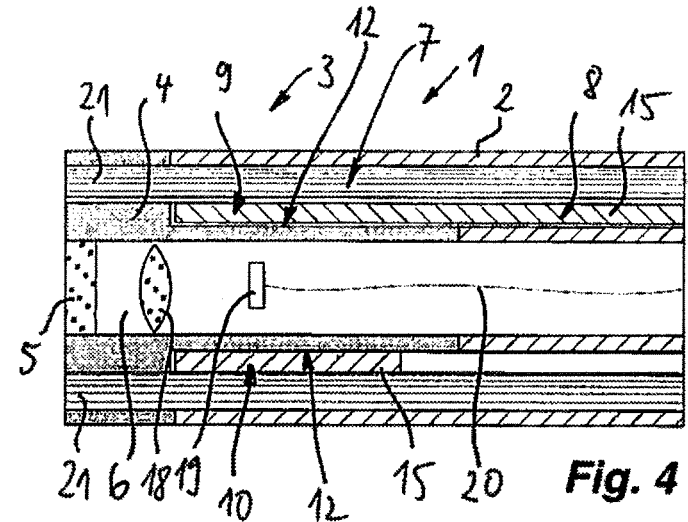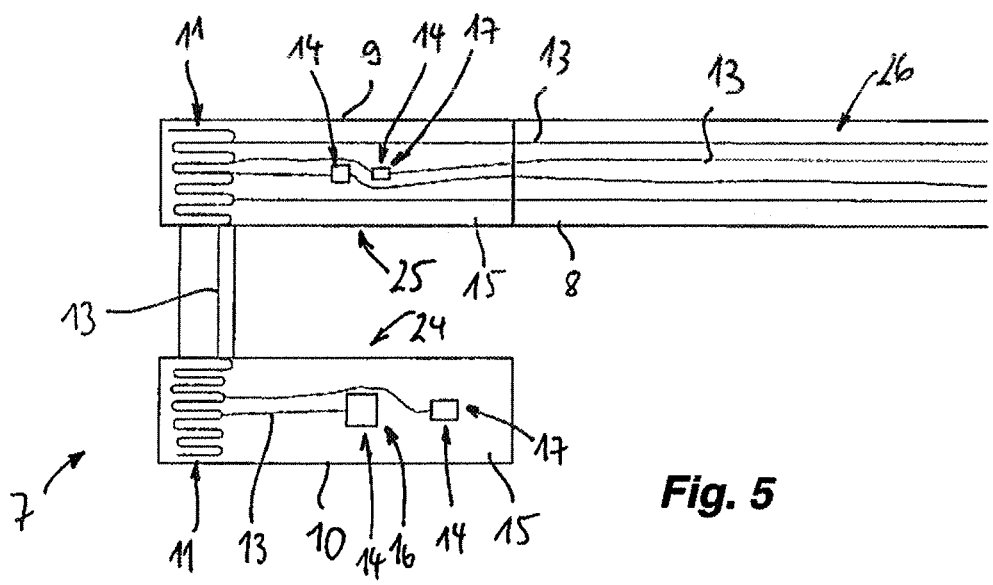

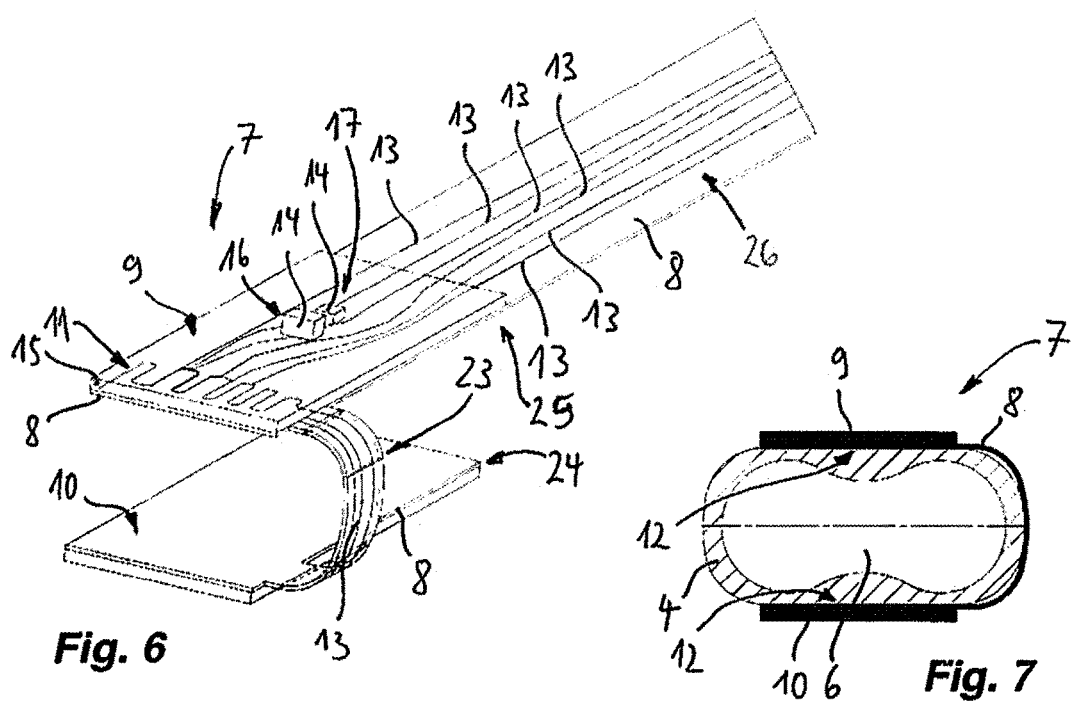
Fig. 6
Fig. 7
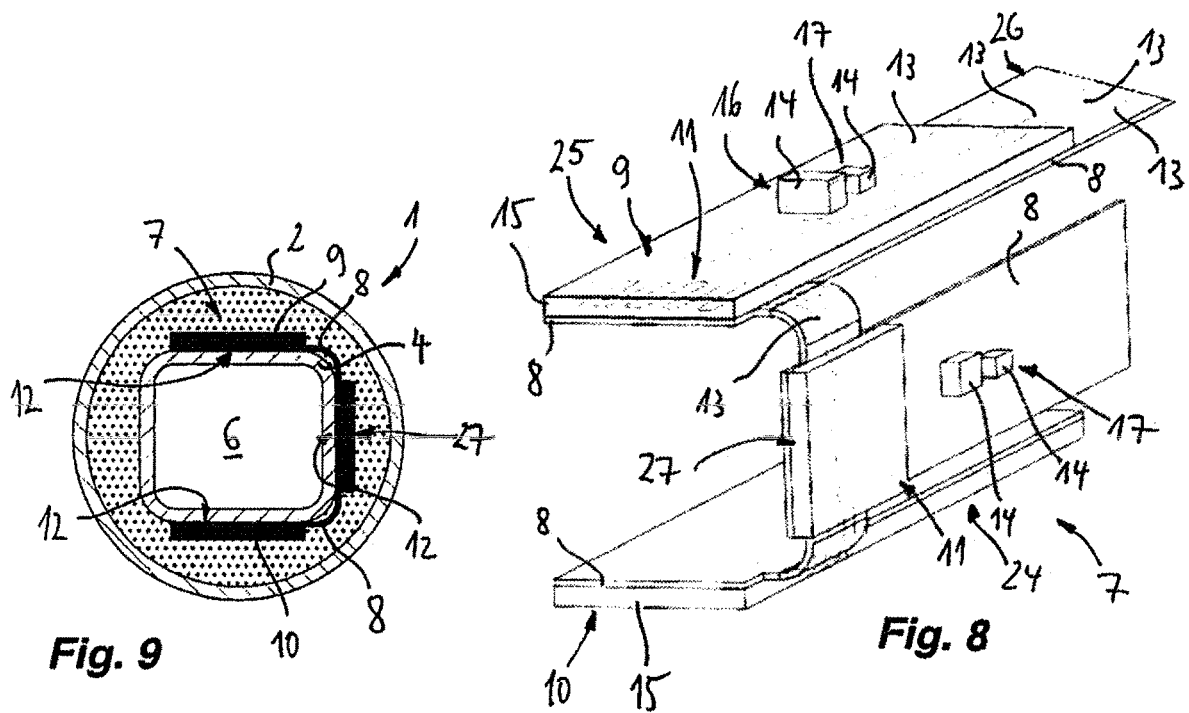
Fig. 9
Fig. 8
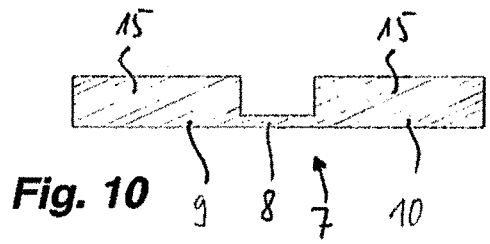
Fig. 10
Fig. 11

ENDOSCOPE

INCORPORATION BY REFERENCE

The following documents are incorporated herein by reference as if fully set forth: German Patent Application No.: 10 2016 001 048.7, filed Jan. 30, 2016.

BACKGROUND

The invention relates to an endoscope with a shaft, at the distal end of which a head part made of a metallic material is formed which carries a plane glass.

Endoscopes of this kind are known and are used, for example, for medical examinations, wherein the plane glass at the distal end of the endoscope forms a seal against entry of moisture.

It has been found during use that, under certain environmental conditions, the plane glass mists up, which reduces the usability of the endoscope.

SUMMARY

The object of the invention is to eliminate the described disadvantage.

The stated object is achieved by the use of one or more features of the invention. In particular, in an endoscope of the type described above, it is thus provided according to the invention that a heating device is formed on a flexible printed circuit board, which is stiffened in at least one area, that a heating element of the heating device is formed in the at least one stiffened area, and that the heating device lies with the stiffened area flat on the head part. It is an advantage in this case that the heating element can be arranged in an area that is mechanically stabilized by the stiffening, which can make production easier and the heating device more robust.

Compared to the solution according to U.S. Pat. No. 8,206,288 B2, for example, in which the use of a heating foil is proposed which is wound in the circumferential direction about an inner tube in the endoscope shaft, the invention thus affords the advantage that it is possible for a planar heating structure to be laid in a defined manner on a planar support surface. This improves the heat transfer and helps avoid misting of the plane glass.

In one embodiment of the invention, provision can be made that a flattening is formed on the head part, on which flattening the heating device bears with the stiffened area. It is an advantage in this case that a defined contact surface is made available for heat transfer. The flattening is preferably planar. This permits the realization of particularly good heat transfer with the lowest possible heat transfer resistance and/or the highest possible heat transfer coefficient.

In one embodiment of the invention, provision can be made that the heating element is formed on a side of the printed circuit board facing away from the head part in the position of use. It is an advantage in this case that a defined support of the stiffened area on the head part can be achieved particularly easily and, in particular, independently of manufacturing tolerances of the heating element.

In one embodiment of the invention, provision can be made that the printed circuit board is coated and/or populated in some areas on both sides. It is an advantage in this case that a greater surface area of the printed circuit board can be utilized.

In one embodiment of the invention, provision can be made that the head part is contacted in a planar manner on at least two sides by the aforementioned or by a respective stiffened area of the heating device. It is advantageous if the head part is contacted on three sides by a stiffened area of the heating device. This permits a thermal connection from three sides, and the head part can be inserted from a fourth side into the heating device, preferably laterally with respect to the longitudinal axis of the shaft. It is particularly advantageous if the heating elements or a heating element are/is formed on a common flexible printed circuit board. This permits simple assembly, since the number of individual parts necessary for the assembly can be kept small. Alternatively or in addition, provision can preferably be made that the heating elements are formed in the common stiffened area, or a heating element is formed in each case in a respective stiffened area. The formation on a common stiffened area permits pre-shaping of the heating device for adaptation to a contour of the head part. The formation in respectively separate areas permits an improved flexibility of the heating device.

In one embodiment of the invention, provision can be made that the heating element is formed from a manganin coating. Manganin can be characterized here as an alloy of copper, nickel and manganese. A composition of 82 to 84% copper, 12 to 15% manganese and 2 to 4% nickel is preferred. Manganin can also be characterized as a resistance alloy. Thus, the heating element can be formed easily on the printed circuit board. It is particularly expedient if the manganin coating is formed extending in a meandering shape. It is an advantage in this case that a great length of the heating element can be obtained within a small space. This permits a high heating power within a small installation space. It is particularly expedient in this case if at least one electrical feed to an electronic component on the printed circuit board and/or to the at least one heating element is formed with a manganin coating. Simple bonding of the heating element or of the heating elements can thus easily be achieved.

In one embodiment of the invention, provision can be made that the stiffened area is formed by a covering. It is particularly expedient in this case if the covering is applied to the at least one heating element or to the aforementioned heating elements or even to all the heating elements. It is an advantage in this case that the heating element or the heating elements are able to be arranged with a covering. In particular, provision can be made that the covering is formed by coating with a glass-fiber-reinforced material and/or polyamide. Stiffening can thus be obtained in a particularly simple way.

In one embodiment of the invention, provision can be made that an electronic drive of the heating device is formed on the printed circuit board. It is thus possible to do without further printed circuit boards. It is particularly expedient if the drive is configured to maintain a predefined maximum temperature on the heating device. It is thus possible to avoid overheating of the head part, which overheating, in a medical application, can cause tissue damage for example or, in an industrial application, can cause damage to materials.

In one embodiment of the invention, provision can be made that at least one imaging lens and/or at least one image sensor is/are arranged in the head part. It is an advantage in this case that an optical image can be captured via the temperature-controlled head part. It is thus possible to avoid, or at least to reduce, impaired imaging caused by misted disks.

In one embodiment of the invention, provision can be made that the shaft accommodates the head part within it.

The head part can thus be used in a manner protected from mechanical stresses. It is particularly expedient in this case if an optical fiber is arranged between the head part and the shaft. It is thus possible to utilize an installation space for feeding light into an examination area.

In one embodiment of the invention, provision can be made that the shaft ends on the head part. The shaft can thus easily be closed at the distal end. It is particularly expedient in this case if the head part has at least one through-opening which is oriented in a longitudinal direction of the shaft and through which an optical fiber extends. A mechanically stable closure of the endoscope at the distal end can thus be achieved which permits illumination of an examination area.

The head part is preferably formed in one piece in the invention. This results in a particularly robust construction.

In one embodiment of the invention, provision can be made that a temperature sensor is arranged on the flexible printed circuit board. It is thus possible to detect an instantaneous operating temperature and/or to monitor for a maximum temperature being exceeded. It is particularly expedient in this case if the temperature sensor is arranged in the stiffened area and/or in a further stiffened area. Alternatively or in addition, the at least one temperature sensor can be arranged at a distance from a heating element, for example from the aforementioned heating element and/or a further heating element, in particular from each heating element. For example, the temperature sensor can be arranged in an end facing away from a bonding of the flexible printed circuit board. Distortion of a temperature measurement caused by currents in the bonding can thus be reduced or even avoided.

In one embodiment of the invention, provision can be made that the flexible printed circuit board has a U-shape when unwound from the head part. It is thus easily possible to create space for receiving additional electronic components, particularly in an area adjoining the head part along the shaft.

In particular, provision can be made in this case that a stiffened area is formed on each limb of the U-shape. An embodiment can thus be formed in which the head part is contacted by two stiffened areas. Preferably, each stiffened area carries a respective heating element. Good temperature control of the head part can be achieved in this way. Provision can also be made that two limbs of the U-shape, in particular the aforementioned limbs, are connected by a flexible connection piece. It is thus possible to provide sufficient flexibility to wind the printed circuit board with the stiffened areas around the head part. A spacing of the stiffened areas from one another can be matched to a spacing of two flattenings along a circumference on the head part. The areas thus match the flattenings without further machining steps.

BRIEF DESCRIPTION OF THE DRAWINGS

The invention is now described in more detail on the basis of illustrative embodiments, although it is not limited to these illustrative embodiments. Further illustrative embodiments are obtained through combination of the features of one or several claims with each other and/or with one or several features of the illustrative embodiments.

In the drawings:

FIG. 1 shows a view of the distal end of an endoscope according to the invention, FIG. 2 shows a longitudinal section through the endoscope according to the invention as shown in FIG. 1, FIG. 3 shows a front view of the distal end of a further endoscope according to the invention, FIG. 4 shows the endoscope according to FIG. 3 in a longitudinal section, FIG. 5 shows a unwound heating device of an endoscope according to FIG. 1 or FIG. 3, FIG. 6 shows the heating device according to FIG. 5 in the position of use before insertion of the head part, FIG. 7 shows the heating device according to FIGS. 5 and 6 with the head part inserted, FIG. 8 shows a further heating device of an endoscope according to the invention with three stiffened areas, FIG. 9 shows a further endoscope according to the invention with the heating device according to FIG. 8, FIG. 10 shows a schematic sectional view through an unwound heating device of an endoscope according to the invention, and FIG. 11 shows a schematic sectional view of a further heating device of an endoscope according to the invention.

DETAILED DESCRIPTION OF THE PREFERRED EMBODIMENTS

FIGS. 1 and 2 are first of all described below.

An endoscope according to the invention, designated overall by reference sign 1, has a shaft 2 extending as far as a distal end 3.

A head part 4, which is produced from a metallic material, is formed on the distal end 3.

The head part 4 carries a plane glass 5. The plane glass 5 seals off an interior 6 of the head part 4 from the outside, in particular in a liquid-tight manner.

The heating device 7 is shown in more detail in FIG. 5. Two stiffened areas 9, 10, in each of which a respective heating element 11 is arranged, are formed on a flexible printed circuit board 8.

FIG. 1 shows the heating device 7 in the position of use, wherein the position of the stiffened areas 9, 10 can be seen. Accordingly, the heating device 7 lies with the stiffened areas 9, 10 flat on the head part 4.

For this purpose, a flattening 12 of the otherwise cylindrical head part is formed on the latter for each stiffened area 9, 10, said flattening 12 having a planar contact face for laying the stiffened area 9, 10 flat on the head part 4.

In the illustrative embodiment according to FIG. 1 and FIG. 2 with FIG. 5, the heating elements 11 are each formed on a side of the printed circuit board 8 which, in the position of use, is oriented toward the outside and thus facing away from the head part 4.

Each heating element 11 is formed as a manganin coating extending in a meandering shape.

Electrical feeds 13 to the heating elements 11 and to further electronic components 14 on the printed circuit board 8 are likewise formed with the manganin coating.

The stiffened areas 9, 10 are each produced by a covering 15 which, in this illustrative embodiment, is made of glass-fiber-reinforced material or a polyamide placed from the outside onto the printed circuit board 8.

An electronic drive 16 of the heating device 7 is formed on the printed circuit board 8, for example with one or several of the electronic components 14, or at another location. This drive 16 is configured to maintain a predefined maximum temperature on the heating device 7. For this purpose, one of the electronic components 14 or several of the electronic components 14 can be designed as temperature sensor 17.

At least one imaging lens 18 and at least one image sensor 19 are arranged in the head part 4 behind the plane glass 5. The image signal received is carried via an image signal line 20 to a proximal end (not shown) of the endoscope 1.

It will be seen from FIG. 2 that the shaft 2 accommodates the head part 4 within it, wherein an optical fiber 21 is arranged in a ring shape between the head part 4 and the shaft 2.

FIG. 3 and FIG. 4 show a further endoscope 1 according to the invention. Structural parts and functional units that are similar or identical in terms of design and/or function to the preceding illustrative embodiment are labeled with the same reference signs and are not described again separately. The statements made with regard to FIGS. 1, 2 and 5 therefore apply correspondingly to FIGS. 3 and 4.

The illustrative embodiment according to FIGS. 3 and 4 differs from the illustrative embodiment according to FIG. 1 and FIG. 2 in that the shaft 2 ends on the head part 4 and is sealed off flush by the head part 4 in the direction of extent of the endoscope 1.

Through-openings 22 are formed on the head part 4, in which through-openings 22 the optical fibers 21 are guided out from the shaft 2 into the open.

The illustrative embodiment according to FIG. 3 and FIG. 4 also differs from the illustrative embodiment according to FIG. 1 and FIG. 2 in that two plane glasses 5 are formed which are offset with respect to each other and behind each of which a respective imaging lens 18 is arranged.

These two optical channels thus formed are each routed to a respective image sensor 19 or to a common image sensor 19 in order to obtain and to transmit a stereoscopic image.

These coupled optical channels can also be formed in the illustrative embodiment according to FIG. 1 and FIG. 2.

FIG. 6 shows the heating device 7 from FIG. 5 in a state prepared for use.

A connection piece 23, which is formed from the printed circuit board 8 and provides a web-like connection between the stiffened areas 9, 10, is bent in order to bring the stiffened areas 9, 10 to their position of use, in which they can lie flat.

It will be seen from FIG. 5 that the heating device 7, and in particular the flexible printed circuit board 8, has a U-shape in a state in which it is unwound from the head part 4.

A stiffened area 9, 10 is here arranged respectively on each limb 24, 25.

A temperature sensor 17 is formed on that limb 24 which faces away from a bonding 26 of the heating device 7.

The illustrative embodiment according to FIG. 7 shows an alternative cross section of a head part 4 in an endoscope 1 according to the invention. Structural parts or functional units that are similar or identical in terms of function and/or design to the preceding illustrative embodiments are labeled with the same reference signs and are not described again separately. The statements made with regard to FIGS. 1 to 6 therefore apply correspondingly to FIG. 7.

It will be seen that the cross section of the head part 4 is particularly suitable for the formation of a stereoscopic endoscope 1 following FIG. 3 and FIG. 4.

FIG. 9 shows a further illustrative embodiment according to the invention of an endoscope, in which a heating device 7 according to FIG. 8 is inserted. Structural parts and functional units that are similar or identical in terms of function and/or design are labeled with the same reference signs and are not described again separately. The statements made with regard to FIGS. 1 to 7 therefore apply correspondingly to FIGS. 8 and 9.

The illustrative embodiment according to FIGS. 8 and 9 differs from the preceding illustrative embodiments in that three stiffened areas 9, 10, 27 are formed, which each carry a heating element 11 and which lie flat on three sides of the head part 4 in the area of flattenings 12.

In further illustrative embodiments, other numbers of stiffened areas and/or heating elements are formed, and/or other arrangements of the stiffened areas 9, 10, 27 on the head part 4 and/or other cross-sectional shapes of the head part 4 are realized.

FIG. 10 and FIG. 11 show schematic cross sections through a heating device 7.

FIG. 10 shows the case where the constructions for stiffening the areas 9, 10, in particular the coating 15 of the flexible printed circuit board 8, are formed on one side, preferably the side facing away from the head part 4.

By contrast, in the illustrative embodiment according to FIG. 11, the printed circuit board 8 is coated and/or populated with components 14 on both sides.

In the endoscope 1 according to the invention, it is proposed to form a heating device 7 with at least one stiffened area 9, 10, 27 on a printed circuit board 8, wherein at least one heating element 11 is arranged in the stiffened area 9, 10, 27, and wherein the heating device 7 is laid flat, from the outside, on a metallic head part 4 at the distal end 3 of the endoscope.

LIST OF REFERENCE SIGNS 1 endoscope
2 shaft
3 distal end
4 head part
5 plane glass
6 interior
7 heating device
8 printed circuit board
9, 10 stiffened area
11 heating element
12 flattening
13 feed
14 electronic component
15 covering
16 drive
17 temperature sensor
18 imaging lens
19 image sensor
20 image signal line
21 optical fiber
22 opening
23 connection piece
24, 25 limb
26 bonding
27 stiffened area

The invention claimed is:
1. An endoscope (1) comprising:
a shaft (2),
a head part (4) at the distal end (3) of the shaft (2), the head part (4) is made of a metallic material and carries a plane glass (5),
a flexible printed circuit board (8) including a heating device (7) formed thereon, the flexible printed circuit board (8) including a flexible connection piece (23) extending between a first stiffened limb (9, 24) and a second stiffened limb (10, 25), the first stiffened limb (9) and the second stiffened limb (10) being spaced apart from each other, the heating device (7) arranged flat on the head part (4), and a first heating element (11) of the heating device (7) is formed in the first stiffened limb (9, 24), and a second heating element (11) of the heating device (7) is formed in the second stiffened limb (10, 25), the second heating element (11) being different than the first heating element (11), wherein an electronic drive (16) of the heating device (7) is formed on the printed circuit board (8).

2. The endoscope (1) as claimed in claim 1, wherein a flattening (12) is formed on the head part (4), and the stiffened limbs (9, 10, 24, 25) supported on said flattening (12).

3. The endoscope (1) as claimed in claim 1, wherein the head part (4) is contacted in a planar manner on at least two sides by the first and second stiffened limbs (9, 10, 24, 25) of the heating device (7).

4. The endoscope (1) as claimed in claim 1, wherein the heating element (11) is formed from a metallic alloy coating.

5. The endoscope (1) as claimed in claim 4, wherein the metallic alloy coating extends in a meandering shape.

6. The endoscope (1) as claimed in claim 1, further comprising an electrical feed (13) to an electronic component (14) on the printed circuit board (8) which is formed with a metallic alloy coating.

7. The endoscope (1) as claimed in claim 1, wherein the stiffened limbs (9, 10, 24, 25) are formed by a covering (15) applied to the first and second heating elements (11).

8. The endoscope (1) as claimed in claim 7, wherein the covering is at least one of a glass-fiber-reinforced material or polyamide.

9. The endoscope (1) as claimed in claim 7, wherein the stiffened limbs (9, 10, 24, 25) are stiffened by the first and second heating elements (11).

10. The endoscope (1) as claimed in claim 1, wherein the electronic drive (16) is configured to maintain a predefined maximum temperature on the heating device (7).

11. The endoscope (1) as claimed in claim 1, wherein at least one of an imaging lens (18) or an image sensor (19) is arranged in the head part (4).

12. The endoscope (1) as claimed in claim 1, wherein the shaft (2) accommodates the head part (4) therein, and an optical fiber (21) is arranged between the head part (4) and the shaft (2).

13. The endoscope (1) as claimed in claim 1, wherein the shaft (2) ends on the head part (4), and the head part (4) has at least one through-opening (22) which is oriented in a longitudinal direction of the shaft (2) and through which an optical fiber (21) is configured to extend.

14. The endoscope (1) as claimed in claim 1, further comprising a temperature sensor (17) arranged on the flexible printed circuit board (8).

15. The endoscope (1) as claimed in claim 1, wherein the flexible printed circuit board (8) has a U-shape when unwound from the head part (4).

16. The endoscope (1) as claimed in claim 1, wherein the printed circuit board (8) is at least one of coated or populated in some areas on both sides thereof.

17. The endoscope (1) as claimed in claim 1, wherein the first heating element (11) is spaced apart from the second heating element (11).

18. The endoscope (1) as claimed in claim 1, wherein an electrical feed (13) is provided to both the heating element (11) on the first stiffened limb (9, 24) and the heating element (11) on the second stiffened limb (10, 25).

19. The endoscope (1) as claimed in claim 1, wherein the first and the second heating elements (11) are formed with a metallic alloy coating.

* * * * *